United States Patent [19]

Stapp

[11] 4,162,363
[45] Jul. 24, 1979

[54] CONVERSION OF DIENES OR MONOOLEFINS TO DIESTERS

[75] Inventor: Paul R. Stapp, Bartlesville, Okla.

[73] Assignee: Phillips Petroleum Company, Bartlesville, Okla.

[21] Appl. No.: 827,641

[22] Filed: Aug. 25, 1977

[51] Int. Cl.$^2$ ............................................. C07C 67/05
[52] U.S. Cl. ..................... 560/246; 252/439;
260/410.6; 260/464; 260/465 D; 260/465.4;
560/1; 560/60; 560/83; 560/84; 560/85;
560/87; 560/89; 560/105; 560/106; 560/111;
560/112; 560/122; 560/125; 560/127; 560/192;
560/193; 560/197; 560/199; 560/228; 560/229;
560/230
[58] Field of Search .................. 560/246, 1, 60, 89,
560/199, 112; 260/410.6, 464, 465 D, 465.4

[56] References Cited

U.S. PATENT DOCUMENTS

| | | | |
|---|---|---|---|
| 2,695,313 | 11/1954 | Toland | 260/530 |
| 2,870,196 | 1/1959 | Barnay | 260/485 |
| 2,903,480 | 9/1959 | Toland | 260/523 |
| 2,985,521 | 5/1961 | Herman | 44/573 |
| 3,119,874 | 1/1964 | Paszthory | 260/497 |
| 3,119,875 | 1/1964 | Steinmetz | 260/604 |
| 3,634,496 | 1/1972 | Kominami | 260/497 |
| 4,026,924 | 5/1977 | Stapp | 560/246 |

FOREIGN PATENT DOCUMENTS 1368505 9/1974 United Kingdom .

OTHER PUBLICATIONS

Suzuki, Ind. and Eng. Chem. Prod. Res. Dev., 10, pp. 179-183 (1973).
Hill, Chem. Rev., 61, pp. 537-562 (1961).

*Primary Examiner*—Bernard Helfin
*Assistant Examiner*—Michael Shippen

[57] ABSTRACT

Conjugated dienes or monoolefins are converted to diesters in a process utilizing a catalyst system comprising an alkali metal compound and a sulfur source comprising elemental sulfur or a sulfur halide, optionally with a halide source, in carboxylic acid media.

41 Claims, No Drawings

CONVERSION OF DIENES OR MONOOLEFINS TO DIESTERS

FIELD OF THE INVENTION

The invention pertains to the conversion of conjugated dienes to diesters. In another aspect, the invention pertains to the conversion of monoolefins to diesters. In a further aspect, the invention pertains to a sulfur-based catalyst system.

BACKGROUND OF THE INVENTION

Conjugated dienes and monoolefins such as butadiene or ethylene, present intriguing possible sources of a variety of more valuable chemicals, valuable intermediates and end-products. Such unsaturated compounds, obtained from various sources such as the conversion of or extraction from refinery streams produced in the modern integrated refinery sometimes termed a petrocomplex, are still relatively cheap chemicals and upgrading thereof has economic advantages.

BRIEF DESCRIPTION OF THE INVENTION

I have discovered that a catalyst system comprising an alkali metal compound and a sulfur source comprising elemental sulfur or sulfur halide, optionally with a halide source, is effective to oxidize in carboxylic acid media an unsaturated reactant selected from conjugated diolefins and monoolefins to diesters.

My process and catalyst system in one aspect provide for the conversion of cyclic or acyclic monoolefins to saturated cyclic or acyclic vicinal diesters. In a further aspect, my process and catalyst system provide for the conversion of cyclic or acyclic conjugated diolefins to unsaturated diesters.

DETAILED DESCRIPTION OF THE INVENTION

Unsaturated Reactant

The unsaturated reactants which can be converted according to my process and catalyst are selected from conjugated dienes and monoolefins. While mixtures of two or more of either or both of these can be employed, preferably and usually single species are employed to limit subsequent purification steps.

The monoolefins can be either acyclic or cyclic, substituted or unsubstituted, and there does not appear to be any operability limitation on molecular size other than convenience and availability.

The acyclic monoolefins, preferably of 2 to 16 carbon atoms per molecule for convenience and availability, correspond to the general formula:

The cyclic monoolefins, preferably of 4 to 16 carbon atoms per molecule for convenience and availability, correspond to the general formula:

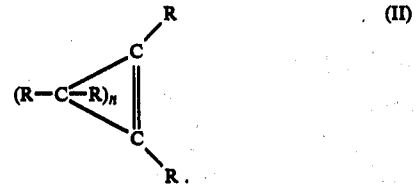

The conjugated diolefin can be either acyclic or cyclic, substituted or unsubstituted, and there does not presently appear to be any limitation on molecular size except convenience and availability.

The acyclic conjugated diolefins, preferably of 4 to 16 carbon atoms per molecule for convenience and availability, correspond to the general formula:

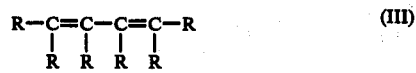

The cyclic conjugated diolefins, preferably of 5 to 16 carbon atoms per molecule for convenience and availability, correspond to the general formula:

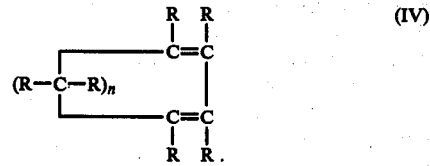

In each of the above formulae, each R is individually selected from hydrogen, halogen, cyano, —COOR', and a hydrocarbyl radical containing preferably not over 12 carbon atoms and which can be alkyl, aryl, cycloalkyl, or combination thereof such as aralkyl, alkaryl, or the like. R' is hydrogen, or an alkyl or aryl radical of preferably not over 10 carbon atoms. The n is an integer of preferably 1 to 14, within the carbon atom limitations described.

Exemplary acyclic monoolefins include ethylene, propylene, 1-butene, 2-butene, 1-hexene, 2-octene, 1-decene, 3-dodecene, 1-hexadecene, 2,3-dimethyl-2-butene, 1,1-diphenylethylene, 1-chloro-2-butene, 3-butenenitrile, ethyl cinnamate, and the like. Exemplary cyclic monoolefins include vinylcyclohexane, cyclobutene, cyclopentene, cyclohexene, cycloheptene, cyclooctene, cyclododecene, 1-methyl-1-cyclopentene, 1-phenyl-1-cyclohexene, ethyl 1-cyclohexene-1-carboxylate, 1,3,4,5,6-pentachlorocyclohexene, 1-cyano-1-cyclohexene, and the like.

Exemplary acyclic conjugated diolefins include: 1,3-butadiene, 2-methyl-1,3-butadiene, 2-chloro-1,3-butadiene, 2-ethyl-1,3-butadiene, 2-cyano-1,3-butadiene, 2-methylene-3-butenoic acid, 2,4-pentadienenitrile, 1,3-hexadecadiene, 2-methoxycarbonyl-1,3-butadiene, 2-decyloxycarbonyl-1,3-butadiene, 2-phenoxycarbonyl-1,3-butadiene, 2-(1-naphthyloxy)carbonyl-1,3-butadiene, 2-benzyl-1,3-butadiene, 2-p-tolyl-1,3-butadiene, 2-chloro-3-methyl-1,3-butadiene, and the like.

Exemplary of the cyclic conjugated diolefins include 1,3-cyclohexadiene, 1,3-cyclooctadiene, 1,3-cyclododecadiene, 5-methyl-1,3-cyclohexadiene, 2,4-cyclohexadiene-1,2-dicarboxylic acid, octafluoro-1,3-cyclohexadiene, hexachlorocyclopentadiene, 5,6,7,8-tetrabromo-1,3-cyclooctadiene, 2-cyclohexyl-1,3- butadiene, 1,3-cyclohexadecadiene, 2-undecyl-1,3-cyclopentadiene, 2-methoxycarbonyl-1,3-cyclooctadiene, 2-decyloxycarbonyl-1,3-cyclopentadiene, 2-phenoxycarbonyl-1,3-cyclohexadiene, 2-(1-naphthyloxy)carbonyl-1,3-cyclopentadiene, 2-benzyl-1,3-cyclooctadiene, 2-p-tolyl-1,3-cyclohexadiene, and the like.

It is presently preferred that either the monoolefin reactant or the conjugated diolefin reactant contain only carbon and hydrogen because of availability and reactivity considerations.

CATALYST SYSTEM

The process of my invention is carried out employing a catalyst system comprising (A) an inorganic sulfur source comprising elemental sulfur, a halide of sulfur, or mixture; and (B) an alkali metal compound, optionally and preferably including a further halide. Presently preferably the catalyst system consists essentially of these components.

The elemental sulfur can be employed in any of its various known forms, though it is presently preferred that a form be utilized which can be easily dispersed in finely divided form in the reaction mixture. Exemplary sulfur halides include sulfur monochloride($S_2Cl_2$), sulfur dichloride($SCl_2$), and sulfur monobromide($S_2Br_2$), and mixtures thereof. Because of convenience in handling, low cost, and availability, elemental sulfur presently is preferred as the sulfur catalyst component.

Any alkali metal compound can be used so long as it is suitable and effective, and is sufficiently soluble in the media as to contribute the desired alkali metal ion. The alkali metal can be one or more of lithium, sodium, potassium, or cesium. Suitable alkali metal compounds include the halides, nitrates, carboxylates, oxides, sulfides, and hydroxides.

Exemplary alkali metal compounds include lithium chloride, lithium bromide, lithium iodide, lithium acetate, lithium benzoate, lithium octadecanoate, lithium oxide, lithium nitrate, lithium sulfide, and the like; as well as the corresponding sodium, potassium, rubidium, and cesium salts; and the like; and mixtures thereof.

It is optional though presently preferred to include in my catalyst system and in my process a source of halide ion, specifically chloride or bromide ion. It presently appears that the halide ion source provides somewhat improved yields of esters obtained in my process. The halide ion can be provided by the sulfur halide component, by the alkali metal compound, or by both, or a separate source of further halide ion can be added to the reaction system. Such additional sources include haloolefin compounds such as the dihalobutenes and allyl halides.

The catalyst of the instant invention can be further described in terms of the ratio of sulfur as free sulfur or the sulfur in the sulfur halide compound to the alkali metal compound component of the catalyst. The ratios can range widely, so long as effective for the oxidation results desired. This ratio can be conveniently expressed in terms of an atom ratio of sulfur to alkali metal. Presently considered exemplary is an atom ratio in the range of about 1:0.1 to 1:20, preferably about 1:1 to 1:8.

The amount of catalyst employed in the process of my invention can be expressed in terms of the molar ratio of unsaturated reactant to gram equivalents of sulfur in the catalyst system. The ratios can range widely, so long as effective for the oxidation results desired. Presently considered exemplary is a ratio in the range of about 1:1 to 50:1, preferably about 2:1 to 12:1.

Where employed, the amount of halide ion source can be expressed in terms of the gram equivalent ratio of halide ion to sulfur in the catalyst system. The ratios can range widely, so long as effective for the oxidation results desired. Presently considered exemplary is a ratio in the range of about 0.1:1 to 20:1, preferably about 1:1 to 10:1.

CARBOXYLIC ACID MEDIA/REACTANT

The term carboxylic acid media includes the use of mono- or dicarboxylic acids alone, or in admixture with each other, or with the anhydrides. The carboxylic acid employed in the process of my invention includes monocarboxylic acids, dicarboxylic acids, or both, preferably of up to 18 carbon atoms per molecule for availability and liquidity under suggested reaction conditions, and most preferably employed in conjunction with an anhydride.

The monocarboxylic acids, preferably of 2 to 18 carbon atoms per molecule, can be characterized by the (V) general formula $R''' - COOH$ in which $R'''$ represents an alkyl, cycloalkyl, or aryl radical, and includes halogen, cyano, and $-COOR'$ substituted derivatives thereof in which up to four halogen, cyano, or $-COOR'$ substituents can be present in the $R'''$ group. $R'$ is as previously defined.

The dicarboxylic acids, preferably of 2 to 18 carbon atoms per molecule, can be characterized by the (VI) general formula $R''''(COOH)_2$ in which $R''''$ represents a valence bond, or is an alkylene, cycloalkylene, or arylene radical, and includes halogen, cyano, and $-COOR'$ derivatives thereof in which up to four halogen, cyano or $-COOR'$ substituents can be present in the $R''''$ group. $R'$ is as previously defined.

Exemplary monocarboxylic acids include acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, 2-bromobutanoic acid, ethyl hydrogen adipate, 4-chlorobenzoic acid, 4-cyanobenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, and the like, alone, or in admixture.

Exemplary dicarboxylic acids include oxalic acid, malonic acid, succinic acid, adipic acid, terephthalic acid, tetrabromo-1,4-benzenedicarboxylic acid, tetracyano-1,4-benzenedicarboxylic acid, tetramethoxycarbonyl-1,4-benzenedicarboxylic acid, 2-decyloxycarbonylhexanedioic acid, and the like, alone, or in admixture.

It is optional, though presently preferred, to employ, as part of the reaction mixture, a carboxylic acid anhydride in addition to the carboxylic acid, preferably the corresponding carboxylic acid anhydride. The use of a carboxylic acid anhydride serves to simplify the purification and separation steps by reducing the amount of by-products which contain free hydroxy groups. Exemplary anhydrides include those corresponding to the described acids and need not be individually recited.

The presently preferred carboxylic acid is acetic acid, and presently preferred is a carboxylic acid media of acetic acid/acetic anhydride.

REACTION CONDITIONS

The process of my invention is an oxidation reaction and as such is carried out in the presence of free oxygen. The amount of oxygen present is not believed to be critical, though it is recognized that an undesirably slow reaction will result if the concentration of oxygen is very low. Pure oxygen can be employed, or mixtures of oxygen with inert gases such as air can be employed as a convenient source of free oxygen for my process.

It is recognized that explosive conditions could be attained if the amount of oxygen added to the reaction system is not properly controlled. The process of my invention, as is true with many oxidation reactions, is highly exothermic and this aspect further dictates caution in adding oxygen to the reaction system. Because of these considerations, it is desirable to add the oxygen incrementally or continuously during the reaction to avoid reaching an explosive range of oxygen concentration, and to allow better control of the temperature of the reaction. A reaction vessel with efficient mixing means thus is desirable to avoid build-up of potentially dangerous concentrations of free oxygen.

The process can be carried out under an oxygen pressurization over a broad range, so long as sufficient oxygen is provided to be effective in the oxidation reactions, not cause unduly long times of reaction, and at the same time not be so unduly high in concentration as to provide unduly hazardous conditions. An exemplary broad range of oxygen pressure is about 0.1 to 1,000, presently preferably about 5 to 200, psig of oxygen above autogenous pressure at the temperature employed.

The reactions of my process can be carried out over a broad temperature range, so long as the temperature is sufficient to provide suitable reactivity of the reactants, and not so high as to be unduly hazardous. Exemplary temperatures lie in the range of about 25° C. to 200° C., presently preferably about 70° C. to 150° C.

The reaction time can range widely, as desired or convenient. The overall reaction time depends on the temperature, catalyst activity, and oxygen pressure employed. An exemplary range is about 0.1 to 12 hours.

The reaction of my invention is carried out in contact with carboxylic acid media/reactant which provides the acyl and/or acyloxy moiety of the final product. Although some diacyloxy olefin product can be obtained using a wide range of ratios of carboxylic acid media to unsaturated reactant, it presently is apparent that the best yields can be obtained when the molar ratio of carboxylic acid reactant to unsaturated reactant is at least about 2:1. In this connection, one mole of the corresponding carboxylic anhydride is equivalent to 2 moles of carboxylic acid. Ratios lower than about 1:1 preferably should not be employed due to reduced yields, and ratios considerably higher than 2:1 can be employed, such as up to about 50:1 or higher, since the excess carboxylic acid media then serves as a reaction diluent. The molar ratio of acid:anhydride, where the anhydride is employed, can range widely so long as effective. A suggested ratio is about 1:2 to 4:1, presently preferred about 2:1, by volume.

The process of my invention can be carried out in a batch or continuous fashion, and in the liquid phase or in the gas phase. In a presently preferred embodiment, the process is carried out in a liquid phase. When conducted in the liquid phase, it is preferred that the carboxylic acid media employed in the process of my invention be normally liquid or at least liquid under the conditions employed for the reaction.

PRODUCT RECOVERY

Reaction mixtures obtained in the process of my invention can be readily treated for product recovery. The reaction mixture generally is vented to remove any unreacted oxygen and unsaturated reactant, and then distilled to remove remaining carboxylic acid media. The product remaining then can be treated, such as by distillation, to recover one or more fractions containing the desired saturated vicinal diesters which will be diacyloxy alkanes or diacyloxy cycloalkanes from monoolefin reactants, or in the case of conjugated diolefin reactants will be diacyloxy olefins as products.

In most instances, the catalyst can be recovered from the distillation residue and recycled to the reaction zone as desired. Any unreacted unsaturated reactant recovered from the reaction mixture also can be recycled to the reaction zone as desired.

The diacyloxy olefins recovered from the product mixture include, in many instances, an amount of 1,2- or vicinal isomer which can be recycled to the reaction zone and thereby converted to the more desirable 1,4-diacyloxy olefin.

PRODUCTS

Saturated cyclic or acyclic vicinal diesters produced from cyclic or acyclic monoolefinic reactants can be represented by general formulae, using reactants as indicated:

| Reactants | | Product |
|---|---|---|
| Carboxylic Acid | Monoolefin | |
| V | I | (VII) |
| | | R–C(R)(O–C(=O)–R'')–C(R)(O–C(=O)–R'') |
| VI | I | (VIII) |
| | | R–C(R)(C(=O)–R''')(CO$_2$H)–C(R)(C(=O)–R''')(CO$_2$H) |

-continued

| Reactants | | Product |
|---|---|---|
| Carboxylic Acid | Monoolefin | |
| V | II | (IX) |

$$\begin{array}{c} R \\ (R-C-R)_n \end{array} \bigg\langle \begin{array}{c} C-O-\overset{O}{\overset{\|}{C}}-R'' \\ C-O-\overset{O}{\overset{\|}{C}}-R'' \\ R \end{array},$$

| VI | II | (X) |

$$\begin{array}{c} R \\ (R-C-R)_n \end{array} \bigg\langle \begin{array}{c} C-O-\overset{O}{\overset{\|}{C}}-R'''-CO_2H \\ C-O-\overset{O}{\overset{\|}{C}}-R'''-CO_2H \\ R \end{array}.$$

Specific examples of saturated cyclic or cyclic vicinal diesters represented by the above formulae include (VII) ethylene diethanoate, ethylene dioctadecanoate, 2,3-butylene bis(2-ethylhexanoate), 1-cyano-2,3-propylene bis(4-chlorobenzoate), and 1,2-hexadecenyl bis(trichloroacetate); (VIII) ethylene di(hydrogen succinate), 1-chloro-2,3-butylene di(hydrogen oxalate); cyclohexylethylene di(hydrogen adipate), 3,4-dodecylene di(hydrogen terephthalate), (IX) 1,2-cyclobutylene diethanoate, 1,2-cyclohexylene bis(chloroacetate), 1,2-cyclododecylene bis(2-bromobutanoate), and 1cyano-1,2-cyclohexylene diethanoate; (X) 1,2-cyclopentylene di(hydrogen malonate), 1,2-cyclooctylene di(hydrogen adipate), 1,2-cyclododecylene di(hydrogen terephthalate), 1-phenyl-1,2-cyclohexylene di(hydrogen oxalate), and 1-methyl-1,2-cyclopentylene di(hydrogen succinate).

Unsaturated diesters produced from cyclic or acyclic conjugated diolefins can be represented by general formulae, using reactants as indicated:

| Reactants | | Product |
|---|---|---|
| Carboxylic Acid | Conjugated Diolefin | Diacyloxy Olefin |
| V | III | (XI) |

$$R-\overset{R}{\underset{\underset{R'''}{\overset{|}{C=O}}}{\overset{|}{C}}}-\overset{R}{C}=\overset{R}{\underset{\underset{R'''}{\overset{|}{C=O}}}{\overset{|}{C}}}-R ,$$

| VI | III | (XII) |

$$R-\overset{R}{\underset{\underset{R''''}{\overset{|}{C=O}}}{\overset{|}{C}}}-\overset{R}{C}=\cdot \\ \overset{|}{CO_2H}$$

| V | IV | (XIII) |

$$(R-C-R)_n \bigg\langle \begin{array}{c} R \\ C \\ \\ C \\ R \end{array} \begin{array}{c} O-\overset{O}{\overset{\|}{C}}-R''' \\ C-R \\ \| \\ C-R \\ O-\overset{O}{\overset{\|}{C}}-R''' \end{array},$$

| VI | IV | (XIV) |

$$(R-C-R)_n \bigg\langle \begin{array}{c} R \\ C \\ \\ C \\ R \end{array} \begin{array}{c} O-\overset{O}{\overset{\|}{C}}-R''''-CO_2H \\ C-R \\ \| \\ C-R \\ O-\overset{O}{\overset{\|}{C}}-R''''-CO_2H \end{array}.$$

General formulae XI, XII, XIII, and XIV represent only the predominant diacyloxy olefin product obtained in the reactions indicated. These products generally are accompanied by relatively smaller amounts of isomeric diacyloxy olefins. For example, using general formula XI as an illustration, the isomeric product can be represented by the general formula:

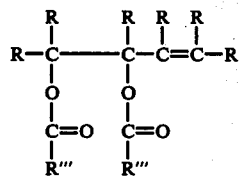

Specific examples of cyclic or acyclic unsaturated diesters represented by the above formulae include (XI) 1,4-diacetoxy-2-butene, 1,4-diacetoxy-2-hexadecene, 1,4-dioctanoyloxy-2-chloro-3-methyl-2-butene, 1,4-di(-trichloroacetoxy)-2-cyano-2-butene, and 1,4-dibenzoyloxy-2-ethoxycarbonyl-2-butene; (XII) 1,4-butene-2-diyl di(hydrogen oxalate), 1,4-butene-2-diyl di(hydrogen adipate), 2-chloro-3-methyl-1,4-butene-2-diyl di(hydrogen succinate), and 1,4-hexadecene-2-diyl di(hydrogen terephthalate); (XIII) 3,5-diacetoxycyclopentene, 3,6-di(chloroacetoxy)cyclohexene, 3,8-di(cyanoacetoxy)cyclooctene, 3,12-diacetoxycyclododecene, 3,8-butanoyloxy-4,5,6,7-tetrabromocyclooctene, and 3,5-di(trichloroacetoxy)hexachlorocyclopentene; (XIV) 3,5-cyclopentenediyl di(hydrogen oxalate), 3,8-cyclooctenediyl di(hydrogen succinate), 3,6-cyclohexenediyl di(hydrogen adipate), and 3,12-cyclododecenediyl di(hydrogen terephthalate).

EXAMPLES

The following examples are intended to assist one skilled in the art to a further understanding of the invention. Particular species, amounts, and relationships, are intended to be exemplary and not limitative of the scope of my invention.

EXAMPLE I

Runs were conducted using a 250 ml Fisher-Porter aerosol compatability bottle equipped with a magnetic stirrer means. In each run the reactor bottle was charged with the catalyst materials, 1,3-butadiene as the unsaturated reactant, and a carboxylic acid media reactant/diluent as indicated in Table I below.

After the bottle reactor was charged with the ingredients it was placed in an oil bath, pressured to 30 psig with oxygen, and heated to 140° C. Typically, about 1.5 hours was required to reach the desired reaction temperature after which the reaction was continued for about 6 hours. During each run the reactor was pressured intermittently with oxygen to 130 psig at about 10–30 minute intervals.

At the conclusion of the reaction the reactor bottle was cooled, vented, and weighed to determine the weight gain (oxygen pick-up) that had occurred during the oxidation reaction. The reaction mixture in each run then was transferred to a distillation flask and distilled through an 18 inch Vigreux column to obtain two fractions. The first fraction was essentially acetic acid or an admixture of acetic acid and acetic anhydride. The second fraction contained small amounts of acetic acid and/or acetic anhydride and the diacyloxy olefins. Gas-liquid phase chromatograph (GLC) analysis of both fractions generally was carried out to identify the components and the amounts present in said fractions. Table I below shows the amounts of catalyst ingredients utilized in each run and other reaction conditions, and Table II presents the results obtained in each run.

Table I

| Run | S, mg-eq. | LiX[a] (mmol) | DHB,[b] (mmol) | AcOH[c] ml | Ac$_2$O[d] ml | 1,3-Bd[e] (mmol) |
|---|---|---|---|---|---|---|
| 1 | 43.7 | LiBr (75) | DBB(10.7) | 50 | 25 | 209.2 |
| 2[f] | 43.7 | LiBr (75) | DBB(10.7) | 50 | 25 | 222.2 |
| 3 | 21.8 | LiBr (112.5) | DBB(10.7) | 50 | 25 | 209.3 |
| 4 | 43.7 | LiBr (75) | DBB(10.7) | 0 | 75 | 225.9 |
| 5[g] | 43.7 | LiBr (75) | DBB(10.7) | 50 | 25 | 212.9 |
| 6 | 43.7 | LiCl (75.3) | DCB(11.3) | 50 | 25 | 210.3 |

[a]LiX = LiBr or LiCl as indicated.
[b]DHB = dihalobutene; DBB is 1,4-dibromo-2-butene, and DCB is 1,4-dichloro-2-butene.
[c]AcOH = acetic acid.
[d]Ac$_2$O = acetic anhydride.
[e]1,3-Bd = 1,3-butadiene.
[f]Run 2 was carried out at 120° C.
[g]Run 5 was carried out with 25 ml acetonitrile added to the reaction mixture and with repressuring with oxygen during the run to 120 psig.

Table II

| Run | 1,2-DAB[h] mmol | c-1,4-DAB[i] mmol | t-1,4-DAB[j] mmol | DAB[k] % Yield |
|---|---|---|---|---|
| 1 | 17.3 | 12.6 | 50.4 | 38.4 |
| 2 | 40.4 | 6.3 | 28.3 | 33.8 |
| 3 | 8.3 | 2.9 | 5.8 | 8.1 |
| 4 | 9.3 | 12.3 | 48.8 | 31.2 |
| 5 | (Not analyzed, apparent low yield) | | | |
| 6 | 6.5 | 1.0 | 3.5 | 5.2 |

[h]1,2-DAB = 1,2-diacetoxy-3-butene.
[i]c-1,4-DAB = cis-1,4-diacetoxy-2-butene.
[j]t-1,4-DAB = trans-1,4-diacetoxy-2-butene.
[k]Yield of combined diacetoxybutenes based on amount of 1,3-butadiene charged.

Cause of the low yields of diacetoxybutenes in Runs 3 and 6 are not presently known. The apparent low yield in Run 5 shows the deleterious effect of including acetonitrile in the reaction mixture. Runs 1, 2, and 4 show good yields of diacetoxybutenes in accordance with my invention.

EXAMPLE II

In the same type of apparatus as employed in the runs of Example I above, another run (Run 7) was carried out in which the reactor was charged with 3.2 grams (75.3 mmol) of lithium chloride, 75 ml of acetic anhydride, 2.8 grams (22.5 mmol) of 1,4-dichloro-2-butene, 3.1 grams (48.4 mmol) of sulfur dioxide, and 11.5 grams (212.9 mmol) of 1,3-butadiene in the vapor phase. The bottle reactor was placed in an oil bath, pressured to 30 psig with oxygen and heated to 140° C. About 1.5 hours were required to reach the desired reaction temperature after which the reaction was continued for 5.5 hours. During the reaction the bottle reactor was pressured to 130 psig with oxygen at about 10–30 minute intervals.

At the end of the reaction the bottle reactor was cooled, vented, and weighed to indicate a weight gain of 2.0 grams. The reaction mixture was transferred, using 14.0 grams of additional acetic anhydride, to a distillation flask and distilled through an 18 inch Vigreux column. The overhead, acetic acid and acetic anhydride, which boiled within a range of 44°–65° C. at 50 mm mercury pressure weighed 89.1 grams, but there was substantially no liquid residue in the flask following the recovery of this overhead material.

Run 7 demonstrates that essentially no formation of diacetoxybutenes occurred in the presence of sulfur dioxide as the sulfur-containing component of the catalyst system.

EXAMPLE III

Runs 8–13 were carried out according to the process of my invention utilizing 1,3-butadiene as the unsaturated reactant, and with elemental sulfur and alkali metal compounds as catalyst. The runs of this Example did not include a source of halide ion in the catalyst system. Run 8 was carried out in the same type of apparatus as described in Examples I and II. Runs 9–13 were carried out in one liter stirred reactors. Run 9 used a glass-lined reactor, and Runs 10–13 used a reactor made of Hastelloy metal. Substantially the same procedure was utilized in each of the runs of this Example as described in Example I.

In Run 9, the reactor was vented, opened, and the reaction mixture transferred to a distillation flask and the acetic acid distilled away at 50 mm mercury pressure. There was recovered 310.5 grams in this distillation as overhead material. The distillation residue was distributed between diethyl ether and water, filtered through Celite to remove some black carbonaceous solid, and the layers separated. The aqueous layer was extracted with diethyl ether and the combined diethyl ether extracts were washed with sodium carbonate solution, dried over anhydrous magnesium sulfate, filtered, and the diethyl ether removed by distillation to give 34.4 grams of an oily material. The acetic acid solution was neutralized with sodium carbonate, dried over anhydrous magnesium sulfate, filtered, and diethyl ether removed to give 14.5 grams of additional oily material. Each of these recovered oily fractions was analyzed by gas-liquid phase chromatography. Results are shown in Table IV.

In Runs 8 and 10–13, the reactor was vented, opened, and the product transferred to a distillation flask. Unreacted 1,3-butadiene was removed at 50 mm mercury pressure followed by the collection of two fractions. Fraction 1 typically boiled from about 40° to 80° C. at 50 mm mercury, while Fraction 2 typically boiled at about 60° to 130° C. at 8 mm mercury. Fraction 1 in each of these runs was essentially acetic acid and/or acetic anhydride, while Fraction 2 consisted essentially of the diacetoxybutenes.

Fraction 2 in each of Runs 8 and 10–13 was analyzed by gas-liquid phase chromatography to determine the composition of said fraction.

Table III shows the amounts of catalyst ingredients and 1,3-butadiene charged in each of the runs along with the reaction conditions. Table IV shows the results obtained in Runs 8–13.

Table III

| Run No. | S mg-eq. | Li Compound mmol | AcOH ml | Ac₂O ml | 1,3-Bd mmol | Temp. °C. |
|---|---|---|---|---|---|---|
| 8 | 43.7 | 75[a] | 0 | 75 | 212.6 | 140 |
| 9 | 81.1 | 225[a] | 75 | 150 | 925.9 | 140 |
| 10 | 81.1 | (23g)[b] | 75 | 150 | 907.4 | 100 |
| 11 | 18.7 | 200[a] + 10[c] | 75 | 150 | 935.2 | 140 |
| 12 | 40.5 | 50[d] | 150 | 75 | 1,037 | 140 |

Table III-continued

| Run No. | S mg-eq. | Li Compound mmol | AcOH ml | Ac₂O ml | 1,3-Bd mmol | Temp. °C. |
|---|---|---|---|---|---|---|
| 13 | 40.5 | [e] | | 150 | 75 | 1,055 | 140 |

[a]Lithium acetate dihydrate.
[b]Lithium acetate (purified). Hydrated state not known.
[c]Lithium nitrate.
[d]Lithium sulfide.
[e]Cupric acetate monohydrate, 50 mmol.

Table IV

| Run No. | 1,2-DAB mmol | c-1,4-DAB mmol | t-1,4-DAB mmol | DAB % Yield |
|---|---|---|---|---|
| 8 | 31.4 | —[f] | 5.1 | 17.2 |
| 9 | 77.8 | 4.8 | 28.7 | 12 |
| 10 | 104.9 | (47.5)[g] | | 16.8 |
| 11 | 82.5 | 3.4 | 9.1 | 10.2 |
| 12 | 76.9 | (25.6)[g] | | 9.9 |
| 13 | (Analysis not conducted due to low yield). | | | |

[f]Not detected in GLC analysis.
[g]Separate determination of cis- and trans- isomer content not carried out.

Comparison of the results of Table IV with those of Table II indicate that it is preferred to utilize a halide ion source in the catalyst system of this invention in order to achieve higher diacetoxybutene yields. The low yield of Run 13 shows that a copper compound is not a suitable replacement for the alkali metal compound catalyst component of my invention.

EXAMPLE IV

Runs 14 and 15 were carried out according to the process of my invention using trans-2-butene as the unsaturated reactant. These runs utilized the one liter glass-lined reactor as the reaction vessel as described in Example III, 150 ml of acetic anhydride and 75 ml of acetic acid as the carboxylic acid media reactant/diluent system, and a catalyst composed of 2.6 grams (81.1 milligram equivalents) of powdered sulfur and 225 mmol of lithium bromide. In each Run 14 and 15 the autoclave was pressured to about 60 psig with oxygen initially and then heated to about 140° C. About 0.75 hours was required to reach the desired reaction temperature after which the reaction was continued for about 3.5 hours. During each run the reactor was re-pressured to about 220 to 350 psig with oxygen at about 30 minute intervals.

At the conclusion of the reaction for Run 14, the autoclave was cooled, vented, and the reaction mixture transferred to a distillation flask and distilled through an 18 inch Vigreux column to recover two fractions. Fraction 1 boiling from 41° to 75° C. at 58 mm mercury pressure weighed 276.8 grams, while Fraction 2 boiling at 75° to 110° C. at 58 mm mercury pressure weighed 39.0 grams. Fraction 2 appeared to contain some acetic acid so it was taken up in diethyl ether, washed with sodium carbonate, and dried over anhydrous magnesium sulfate and then filtered. The diethyl ether was removed by distillation to give 28.2 grams of a pale yellow oil. Fraction No. 1 also was neutralized with sodium carbonate and then extracted into diethyl ether. The diethyl ether extracts were dried over anhydrous magnesium sulfate, filtered, and the diethyl ether removed by distillation to give 34.8 grams of pale yellow oil. Each of the oily residues from the fractions above were analyzed by gas-liquid phase chromatography combined with mass spectral analysis.

The reaction mixture obtained in Run 15 was treated in essentially the same manner as that described for Run 14 with the exception that the second fraction obtained on the initial distillation was not treated with diethyl ether. The products recovered from the diethyl ether extraction of sodium carbonate neutralized fraction 1 and fraction 2 were analyzed as described for the products of Run 14 above. The results of Runs 14 and 15 are shown below in Table V.

Table V

| Run No. | trans-2-Butene mmol | 2,3-DABA[a] mmol | % Yield[b] 2,3-DABA |
|---|---|---|---|
| 14 | 910.7 | 115 | 12.6 |
| 15 | 910.7 | 88 | 9.6 |

[a] 2,3-DABA = 2,3-diacetoxybutane.
[b] Yield based on the amount of trans-2-butene charged. The product mixtures also contained amounts of other compounds such as dibromobutanes (4–8 grams), butenyl acetates (1–4 grams), and unidentified compounds (1–4 grams).

The results shown in Table V demonstrate that the catalyst system of my invention is effective for the production of diacyloxyalkanes from 1-olefins, here diacetoxybutanes from butenes, in the presence of free oxygen and carboxylic acid media, here acetic acid admixed with acetic anhydride. Unreacted unsaturated reactant can be recovered and recycled, if desired.

UTILITY

The 1,4-diacyloxy olefins have utility as intermediates for the preparation of the corresponding saturated diols, or tetrahydrofuran or substituted tetrahydrofurans. For example, British Pat. No. 1,170,222 describes the preparation of tetrahydrofurans by starting with conjugated diolefins and proceeding through the 1,4-diacyloxybutenes. Tetrahydrofuran itself has wide utility as a solvent, as a randomizing agent in preparation of various copolymers, and the like. The diols prepared from the process of my reaction are useful for conversion to polyesters or polyurethanes, and as solvents or humectants. The substituted tetrahydrofurans are useful as solvents and intermediates in the preparation of diamines or dicarboxylic acids for polyamide preparation.

Starting with the cyclic or acyclic monoolefins, the resulting products in accordance with the process of my invention are saturated cyclic or acyclic vicinal diesters. These diesters also can be utilized to provide the resulting corresponding diols, which then are saturated vicinal diols, useful as solvents, humectants, monomers for production of polyesters, or polyurethanes, and the like.

The disclosure, including data, has illustrated the value and effectivness of my invention. The examples, the knowledge and background of the field of the invention and the general principles in chemistry and other applicable sciences, have formed the bases to which the broad description of the invention, including the ranges of conditions and generic groups of operant components have been developed, and have formed the bases for my claims here appended.

I claim:

1. A process for the production of diesters which comprises:
   reacting at least one unsaturated reactant selected from conjugated diolefins and monoolefins with oxygen and a carboxylic acid reactant media employing a catalyst system comprising (A) a sulfur source and (B) an alkali metal compound, optionally (C) with a halide source;
   wherein said unsaturated reactant is selected from unsubstituted and substituted diolefins and monoolefins wherein the substituents are selected from the group consisting of halogen, cyano, —COOR', and hydrocarbyl radicals, wherein R' is hydrogen or an alkyl or aryl radical,
   said carboxylic acid media is selected from the group consisting of mono- and dicarboxylic aliphatic and aromatic acids and mixtures with acid anhydrides, having 2 to 18 carbon atoms per molecule,
   said (A) sulfur source is sulfur, sulfur chloride, sulfur bromide or mixture;
   said (B) alkali metal compound is a halide, nitrate, carboxylate, oxide, sulfide, or hydroxide, or lithium, sodium, potassium, or cesium, including mixtures; and
   wherein said optional (C) halide source is a chloride, bromide, or mixture, and is a media soluble said (A) or (B) wherein said (A) or (B) is the halide, or is a haloolefin.

2. The process of claim 1 wherein said unsaturated reactant is a monoolefin and is an acylic monoolefin of 2 to 16 carbon atoms per molecule, and said diester comprises diacyloxy alkanes.

3. The process according to claim 2 wherein said acyclic monoolefin is ethylene, propylene, 1-butene, 2-butene, 1-hexene, 2-octene, 1-decene, 3-dodecene, 1-hexadecene, 2,3-dimethyl-2-butene, vinylcyclohexane, 1,1-diphenylethylene, 1-chloro-2-butene, 3-butenenitrile, or ethyl cinnamate.

4. The process of claim 1 wherein said unsaturated reactant is a monoolefin and is a cyclic monoolefin of 4 to 16 carbon atoms per molecule, and said diester comprises diacyloxy cycloalkanes.

5. The process of claim 4 wherein said cyclic monoolefin is cyclobutene, cyclopentene, cyclohexene, cycloheptene, cyclooctene, cyclododecene, 1-methyl-1-cyclopentene, 1-phenyl-1-cyclohexene, ethyl 1-cyclohexene-1-carboxylate, 1,3,4,5,6-pentachlorocyclohexene, or 1-cyano-1-cyclohexene.

6. The process of claim 1 wherein said unsaturated reactant is a conjugated diolefin and is an acyclic conjugated diolefin of 4 to 16 carbon atoms per molecule, and said diester comprises diacyloxy acyclic olefins.

7. The process according to claim 6 wherein said acyclic conjugated diolefin is 1,3-butadiene, 2-methyl-1,3-butadiene, 2-chloro-1,3-butadiene, 2-ethyl-1,3-butadiene, 2-cyano-1,3-butadiene, 2-methylene-3-butenoic acid, 2,4-pentadienenitrile, 1,3-hexadecadiene, 2-methoxycarbonyl-1,3-butadiene, 2-decyloxycarbonyl-1,3-butadiene, 2-phenoxycarbonyl-1,3-butadiene, 2-(1-naphthyloxy)carbonyl-1,3-butadiene, 2-benzyl-1,3-butadiene, 2-p-tolyl-1,3-butadiene, or 2-chloro-3-methyl-1,3-butadiene.

8. The process of claim 1 wherein said unsaturated reactant is said conjugated diolefin and is a cyclic conjugated diolefin of 5 to 16 carbon atoms per molecule, and said diester comprises diacyloxy cyclic olefins.

9. The process according to claim 8 wherein said cyclic conjugated diolefin is 1,3-cyclohexadiene, 1,3-cyclooctadiene, 1,3-cyclododecadiene, 5-methyl-1,3-cyclohexadiene, 2,4-cyclohexadiene-1,2-dicarboxylic acid, octafluoro-1,3-cyclohexadiene, hexachlorocyclopentadiene, 5,6,7,8-tetrabromo-1,3-cyclooctadiene, 1,3-cyclohexadecadiene, 2-undecyl-1,3-cyclopentadiene, 2-methoxycarbonyl-1,3-cyclooctadiene, 2-decyloxycarbonyl-1,3-cyclopentadiene, 2-phenoxycarbonyl-1,3-cyclohexadiene, 2-(1-naphthyloxy)carbonyl-1,3-cyclopentadiene, 2-benzyl-1,3-cyclooctadiene, or 2-p-tolyl-1,3-cyclohexadiene.

10. The process of claim 1 wherein said catalyst includes said halide source, and said halide source is selected from the group consisting of dihalobutenes and allyl halides.

11. The process of claim 1 employing said halide source wherein said halide is at least in part provided by at least one alkali metal halide.

12. The process of claim 1 wherein said carboxylic acid reactant media monocarboxylic acid is represented by R'''—COOH, and said dicarboxylic acid is represented by R''''(COOH)$_2$, wherein R''' is selected from the group consisting of alkyl, cycloalkyl, and aryl radicals, and halogen, cyano, and —COOR' substituted derivatives thereof, wherein up to four of said halogen, cyano, or —COOR' substituents can be present in said R''' radical; R'''' is selected from the group consisting of a valence bond and alkylene, cycloalkylene, and arylene radicals, and halogen, cyano, and —COOR' substituted derivatives thereof wherein up to four of said halogen, cyano, or —COOR' substituents can be present in said R'''' radical; and R' is selected from the group consisting of hydrogen, an alkyl radical of up to 10 carbon atoms, and an aryl radical of up to 10 carbon atoms.

13. The process of claim 12 wherein said carboxylic acid reactant media comprises said monocarboxylic acid, optionally with said anhydride, and is selected from the group consisting of acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, 2-bromobutanoic acid, ethyl hydrogen adipate, 4-chlorobenzoic acid, 4-cyanobenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, and mixtures.

14. The process of claim 12 wherein said carboxylic acid reactant media comprises said dicarboxylic acid, optionally with said anhydride, and is selected from the group consisting of oxalic acid, malonic acid, succinic acid, adipic acid, terephthalic acid, tetrabromo-1,4-benzenedicarboxylic acid, tetracyano-1,4-benzenedicarboxylic acid, tetramethoxycarbonyl-1,4-benzenedicarboxylic acid, 2-decyloxycarbonylhexanedioic acid, and mixtures.

15. The process of claim 12 employing said sulfur source in the range of about 1:0.1 to 1:20 atom ratio of sulfur to alkali metal, about 1:1 to 50:1 molar ratio of unsaturated reactant to gram equivalents of sulfur, and where halide source is employed said halide source is employed in a ratio of about 0.1:1 to 20:1 gram equivalent ratio of halide ion to sulfur.

16. The process of claim 15 employing a contacting temperature in the range of about 5° to about 200° C. at an oxygen pressure in the range of 0.1 to 1000 psig above autogenous pressure at the temperature employed.

17. The process of claim 15 employing about 1:1 to 1:8 atom ratio to sulfur to alkali metal, about 2:1 to 12:1 molar ratio of unsaturated reactant to gram equivalents of sulfur, and, where employed, about 1:1 to 10:1 gram equivalent ratio of halide ion to sulfur.

18. The process of claim 17 wherein said temperature is in the range of about 70° C. to 150° C., and said oxygen pressure is in the range of about 5 to 200 psig above autogenous.

19. The process of claim 16 employing the carboxylic acid anhydride corresponding to the carboxylic acid employed.

20. The process of claim 16 wherein said reaction is conducted in the liquid phase.

21. The process according to claim 1 wherein when said sulfur source employs said sulfur halide, said sulfur halide is sulfur monochloride, sulfur dichloride, or sulfur monobromide.

22. The process according to claim 15 wherein said alkali metal compound is lithium, sodium, potassium, rubidium, or cesium chloride, bromide, iodide, acetate, benzoate, oxide, octadecanoate, nitrate, or mixture.

23. The process according to claim 18 wherein said unsaturated reactant is a conjugated diolefin and is an acyclic hydrocarbon diolefin, and said carboxylic acid reactant media is a mixture of a monocarboxylic acid and its corresponding anhydride in a volume ratio of about 1:2 to 4:1.

24. The process according to claim 23 wherein said sulfur source is sulfur, said alkali metal compound is lithium bromide, said conjugated diolefin is 1,3-butadiene, further employing said halide source which is 1,4-dibromo-2-butene, said carboxylic acid reactant media comprises acetic acid and acetic anhydride, and the resulting product mixture comprises 1,2-diacetoxy-3-butene, cis-1,4-diacetoxy-2-butene, and trans-1,4-diacetoxy-2-butene.

25. The process according to claim 23 wherein said sulfur source is sulfur, said alkali metal compound is lithium chloride, said conjugated diolefin is 1,3-butadiene, further employing said halide source which is 1,4-dichloro-2-butene, said carboxylic acid reactant media comprises acetic acid and acetic anhydride, and the resulting product mixture comprises 1,2-diacetoxy-3-butene, cis-1,4-diacetoxy-2-butene, and trans-1,4-diacetoxy-2-butene.

26. The process according to claim 23 wherein said sulfur source is sulfur, said alkali metal compound is lithium acetate, said conjugated diolefin is 1,3-butadiene, said carboxylic acid reactant media comprises acetic acid and acetic anhydride, and the resulting product mixture comprises 1,2-diacetoxy-3-butene, cis-1,4-diacetoxy-2-butene, and trans-1,4-diacetoxy-2-butene.

27. The process according to claim 23 wherein said sulfur source is sulfur, said alkali metal compound is lithium nitrate, said conjugated diolefin is 1,3-butadiene, said carboxylic acid reactant media comprises acetic acid and acetic anhydride, and the resulting product mixture comprises 1,2-diacetoxy-3-butene, cis-1,4-diacetoxy-2-butene, and trans-1,4-diacetoxy-2-butene.

28. The process according to claim 23 wherein said sulfur source is sulfur, said alkali metal compound is lithium sulfide, said conjugated diolefin is 1,3-butadiene, said carboxylic acid reactant media comprises acetic acid and acetic anhydride, and the resulting product mixture comprises 1,2-diacetoxy-3-butene, cis-1,4-diacetoxy-2-butene, and trans-1,4-diacetoxy-2-butene.

29. The process according to claim 18 wherein said unsaturated reactant is a monoolefin and is an acyclic monoolefin, and said carboxylic acid reactant media is a mixture of a monocarboxylic acid and its corresponding anhydride in a volume ratio of about 1:2 to 4:1 acid:anhydride.

30. The process according to claim 29 wherein said acyclic monoolefin is 2-butene, said sulfur source is sulfur, said alkali metal compound is lithium bromide, said carboxylic acid reactant media is acetic acid and acetic anhydride, and the resulting product mixture comprises 2,3-diacetoxybutane.

31. The process of claim 12 wherein said unsaturated reactant is a monoolefin and the resulting diesters are represented by:

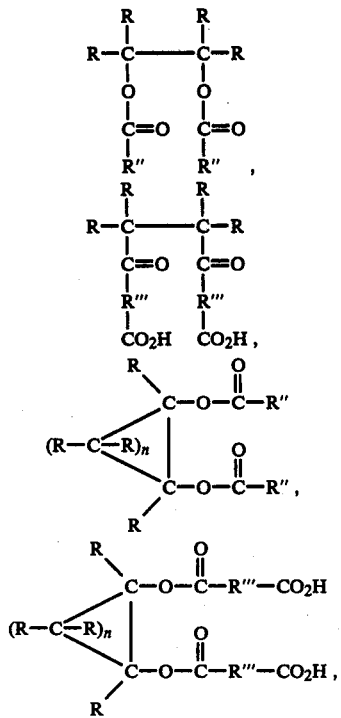

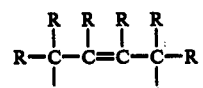

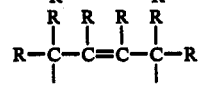

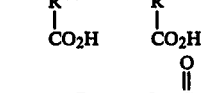

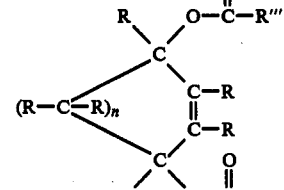

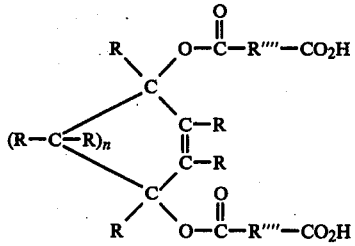

wherein each R is individually selected from hydrogen, halogen, cyano, —COOR'; and a hydrocarbyl radical of up to 12 carbon atoms, and n is an integer of 1 to 14.

32. The process of claim 31 wherein said resulting diester products comprise ethylene diethanoate, ethylene dioctadecanoate, 2,3-butylene bis(2-ethylhexanoate), or 1-cyano-2,3-propylene bis(4-chlorobenzoate) or 1,2-hexadecenyl bis(trichloroacetate).

33. The process of claim 31 wherein said resulting diester products comprise ethylene di(hydrogen succinate), or 1-chloro-2,3-butylene di(hydrogen oxalate).

34. The process of claim 31 wherein said resulting diester products comprise 1,2-cyclobutylene diethanoate, 1,2-cyclohexylene bis(chloroacetate), 1,2-cyclododecylene bis(2-bromobutanoate), 1-cyano-1,2-cyclohexylene diethanoate.

35. The process of claim 31 wherein said resulting diester products comprise cyclohexylethylene di(hydrogen adipate), 3,4-dodecylene di(hydrogen terephthalate), 1,2-cyclopentylene di(hydrogen malonate), 1,2-cyclooctylene di(hydrogen adipate), 1,2-cyclododecylene di(hydrogen terephthalate), or 1-phenyl-1,2-cyclohexylene di(hydrogen oxalate).

36. The process of claim 12 wherein said unsaturated reactant is a conjugated diolefin and the resulting diacyloxy olefins are represented by:

wherein each R is individually selected from hydrogen, halogen, cyano, —COOR'; and a hydrocarbyl radical of up to 12 carbon atoms, and n is an integer of 1 to 14.

37. The process according to claim 36 wherein said diacyloxy olefins are recovered from the resulting reaction product mixture, and any 1,2 or vicinal isomers are recycled to the reaction zone for further conversion to 1,4-diacyloxy olefin.

38. The process of claim 36 wherein the products comprise 1,4-diacetoxy-2-butene, 1,4-diacetoxy-2-hexadecene, 1,4-dioctanoyloxy-2-chloro-3-methyl-2-butene, 1,4-di(trichloroacetoxy)-2-cyano-2-butene, or 1,4-dibenzoyloxy-2-ethoxycarbonyl-2-butene.

39. The process of claim 36 wherein the products comprise 3,5-diacetoxycyclopentene, 3,6-di(chloroacetoxy)cyclohexene, 3,8-di(cyanoacetoxy)cyclooctene, 3,12-diacetoxycyclododecene, 3,8-butanoyloxy-4,5,6,7-tetrabromocyclooctene, or 3,5-di(trichloroacetoxy)hexachlorocyclopentene.

40. The process of claim 36 wherein the products comprise 1,4-butene-2-diyl di(hydrogen oxalate), 1,4-butene-2-diyl di(hydrogen adipate), 2-chloro-3-methyl-1,4-butene-2-diyl di(hydrogen succinate), or 1,4-hexadecene-2-diyl di(hydrogen terephthalate).

41. The process of claim 36 wherein the products comprise 3,5-cyclopentenediyl di(hydrogen oxalate), 3,8-cyclooctenediyl di(hydrogen succinate), 3,6-cyclohexenediyl di(hydrogen adipate), or 3,12-cyclododecenediyl di(hydrogen terephthalate).

* * * * *

UNITED STATES PATENT AND TRADEMARK OFFICE
CERTIFICATE OF CORRECTION

PATENT NO. : 4,162,363

DATED : July 24, 1979

INVENTOR(S) : Paul R. Stapp

It is certified that error appears in the above-identified patent and that said Letters Patent are hereby corrected as shown below:

Col. 15, line 58, Claim 16 (second line), "5°" should be --- 25 ---

Col. 15, line 63, Claim 17 (second line), after "ratio" and before "sulfur", "to" should be --- of ---

Signed and Sealed this

Thirteenth Day of November 1979

[SEAL]

Attest:

RUTH C. MASON
Attesting Officer

LUTRELLE F. PARKER
Acting Commissioner of Patents and Trademarks